United States Patent [19]

Ku et al.

[11] Patent Number: 4,975,467
[45] Date of Patent: Dec. 4, 1990

[54] METHOD OF INHIBITING INTERLEUKIN-1 RELEASE AND ALLEVIATING INTERLEUKIN-1 MEDIATED CONDITIONS

[75] Inventors: George Ku, Cincinnati; Niall Doherty, West Chester, both of Ohio

[73] Assignee: Merrell Dow Pharmaceuticals Inc., Cincinnati, Ohio

[21] Appl. No.: 499,567

[22] Filed: Mar. 26, 1990

Related U.S. Application Data

[63] Continuation of Ser. No. 387,389, Jul. 28, 1989, abandoned, Continuation of Ser. No. 151,572, Feb. 18, 1988, abandoned, which is a continuation-in-part of Ser. No. 26,586, Mar. 17, 1987, abandoned.

[51] Int. Cl.$^5$ ............................................. A61U 31/10
[52] U.S. Cl. ..................................................... 514/712
[58] Field of Search ......................................... 514/712

[56] References Cited

U.S. PATENT DOCUMENTS

| | | | |
|---|---|---|---|
| 3,576,883 | 4/1971 | Neuworth | 260/609 |
| 3,704,327 | 11/1972 | Neuworth | 260/609 |
| 3,786,100 | 1/1974 | Neuworth | 260/590 |
| 3,862,332 | 1/1975 | Barnhart et al. | 424/337 |
| 3,897,500 | 7/1975 | Neuworth | 260/609 |
| 4,560,799 | 12/1985 | Spivack et al. | 524/331 |
| 4,612,341 | 9/1986 | Spivack et al. | 524/331 |

FOREIGN PATENT DOCUMENTS

| | | |
|---|---|---|
| 2417671 | 10/1975 | Fed. Rep. of Germany . |
| 1199871 | 7/1970 | United Kingdom . |

OTHER PUBLICATIONS

Tawara, et al. Japan J. Pharmacol. 41, 211–222 (1986).
Yamamoto, et al. Atherosclerosis 62, 209 (1986).
Comal, et al. Drug Dev. Res. 6, 113(1985).
Beaumont, et al. Artery 10, 71(1982).
Yoshino, et al. The Lancet 2, 740–741 (Sep. 27, 1986).
Naruszewicz, et al. J. Lippid Res. 25, 1206 (1984).
Parthasarathy, et al. J. Clin. Invest. 77, 641(1985).
Carew, et al. Proc. Natl. Acad. Sci. U.S.A. 84, 7725, (Nov. 1987).
Ku, et al. Amer. J. Cardiology 62, 77B, (Jul. 1988).
Drash, et al. Amer. J. Cardiology 62, 27B (Jul. 1988).
Neuworth et al., J. Med Chem., 13, 722 (1970).
Ku, Abstract, Second International Conference on Hypercholesterolemia, Los Angeles, CA, Nov. 13–14, 1987.
Steinberg, ibid.
Kita, ibid.
Chisolm, ibid.
Carew et al., Proc. Natl. Acad. Sci. U.S.A., 84, 7725–7729 (1987).
Kita et al., Proc. Natl. Acad. Sci. U.S.A., 84, 5928–5931 (1987).
Marx, Science, 239, 257–258 (1988).
Libby et al., Fed. Proc., 46, No. 3,975, Abstract 3837 (1987).
Pukel et al., Diabetes, 37, 133–136 (1988).
Mandrup-Poulsen et al., J. Immunol., 139, 4077–4082 (1987).
Roe, Geriatrics, pp. 174–182 (1966).
Skinner et al., Arch. Dermatol, 118, 144 (1982)
Innes and Davidson Defensive Publication No. T960003.
Physician's Desk Reference, 41st Edition, 1357–1359 (1987).
Naruszewicz et al., Journal of Lipid Research, 25, 1206 (1984).
Parthasarathy et al., J. Clin. Invest., 77, 641 (1985).
Murphy, Brit. Journal of Rheumatology, 24(1): 6–9 (1985).
Oppenheim et al., Immunology Today, 2, 45–55 (1986).
Billingham, Brit. J. Rheumatology, 24(1):25–28 (1985).
Dayer, Brit. J. Rheumatology, 24(1):15–20 (1985).
Whicher, Brit. J. Rheumatology, 24(1):21–24 (1985).
Pettipher et al., Proc. Natl. Acad. Sci.(U.S.A.), 83, 8749–8753 (Nov. 1986).
Ristow, Proc. Natl. Acad. Sci. (U.S.A.), 84, 1940–1944 (Apr 1987).
Bendtzen et al., Science, 232, 1545–1547 (Jun. 20, 1986).
Camp et al., The Journal of Immunology, 137(11), 3469–3474 (Dec. 1986).
Kent, Geriatrics, 32(1):127–136 (1977).
Feldman et al., Parasite Immunology, 7, 567–573 (1985).
Phan et al., AJP, 124(2), 343–351 (1986).
Kunkel et al., Biochemical and Biophysical Research Comm., 128(2), 892–897 (1985).
Montecchi et al., J. Pharmacol, 15(4), 481 (1984).
Pharmaprojects, 12, 674 (1982).

Primary Examiner—Stanley J. Friedman
Attorney, Agent, or Firm—Louis J. Wille

[57] ABSTRACT

Methods useful for inhibiting the release of Interleukin-1 and for alleviating interleukin-1 mediated conditions, such as IL-1 mediated inflammation, comprising administration of an effective amount of an alkylidenedithiobis(substituted)phenol, preferably, 4,4'-(isopropylidenedithio(bis(2,6-di-tert-butyl) phenol, generically known as probucol.

20 Claims, No Drawings

METHOD OF INHIBITING INTERLEUKIN-1 RELEASE AND ALLEVIATING INTERLEUKIN-1 MEDIATED CONDITIONS

CROSS-REFERENCE TO RELATED APPLICATION

This is a continuation of application Ser. No. 387,389, filed July 28, 1989, abandoned, which is a continuation of application Ser. No. 151,572, filed Feb. 18, 1988, abandoned, which is a continuation-in-part of application Ser. No. 026,586, filed Mar. 17, 1987, abandoned.

BACKGROUND OF THE INVENTION

1. Field of the Invention

The substituted alkylidenedithio-bis-(substituted)-phenols used in the invention are compounds of the type disclosed in U.S. Pat. Nos. 3,576,883, 3,786,100, 3,862,332 and 3,897,500 and can be made by the methods disclosed in those patents. One of the alkylidenedithio-bis(substituted)phenols, 4,4'-(isopropylidenedithio)bis(2,6-di-tert-butyl) phenol), is known by the generic name "probucol", and is used as a hypocholesterolemic drug. Probucol is known to lower serum cholesterol, and to reduce both high density lipoprotein (HDL) and low density lipoprotein (LDL) cholesterol. It has been shown to inhibit oxidative modification of LDL, an effect which has been hypothesized as possibly inhibiting atherogenesis. Naruszewicz et al., *Journal of Lipid Research*, Vol. 25, 1206 (1984); and Parthasarathy et al., *J.Clin.Invest.*, Vol. 77, 641 (1985).

Interleukin-1 (IL-1) is the name for a family of molecules which have multiple biological effects. The name interleukin-1 was proposed in 1979: and earlier literature reports refer to it by some other name. Murphy, *British Journal of Rheumatology*, 1985; 24(suppl 1): 6–9, and Oppenheim et al., *Immunology Today*, Vol. 2, 45–55 (1986). IL-1 is secreted by stimulated macrophages, and has several significant biological effects, such as mediation of T-lymphocyte proliferation and pyrogenic and proinflammatory effects.

IL-1 activities are summarized in the two above papers. IL-1 has been described to mediate the acute phase response in inflammation, and to have pyrogenic and proinflammatory effects IL-1 induces connective tissue changes, and has been demonstrated to induce the release of degradative enzymes from mesenchymal cells that are present at the sites of bony erosion in inflammatory disease states, such as rheumatoid arthritis. Billingham, *Brit.J.Rheumatology*, 1985:24(suppl 1):25–28. Dayer. *Brit.J. Rheumatology*, 1985:24(suppl 1):15–20. The production of acute phase proteins in the hepatocytes during the acute phase of inflammation is mediated by IL-1 and other cytokines, such as IL-6. Whicher, *Brit.J.Rheumatology*, 1985:24(suppl 1):21–24.

IL-1 is also involved as a mediator in the inflammatory skin disease, psoriasis. Camp et al., J. Immunology 1986: 137: 3469–3474, and Ristow, Proc. Natl. Acad. Sci. U.S.A. 1987: 84: 1940–1944. It is cytotoxic for insulin producing beta cells in the pancreas, and is thus a causative factor in the development of some forms of diabetes mellitus. Bendtzen et al., Science 1986: 232: 1545–1547 and Marx, Science 1988: 239: 257–258, IL-1 also appears to be involved in the development of atherosclerotic lesions or atherosclerotic plaque. Marx, Science 1988: 239: 257–258. IL-1 stimulates growth and proliferation of vascular smooth muscle cells, an effect which is greater in the absence or suppression of endogenous prostaglandins, which could lead to thickening of vascular walls, such as occurs in atherogenesis. Libby et al., Fed. Proc. Mar. 1, 1987: Vol. 46, no. 3: 975, Abstract 3837.

It would be advantageous to control the release of IL-1, and to be able to treat IL-1-mediated effects It would also be advantageous to control or treat IL-1 mediated inflammation, without production of concomitant side effects known to accompany the use of antiinflammatory steroids and non-steroidal antiinflammatory agents.

SUMMARY OF THE INVENTION

It has now been found that substituted alkylidenedithiobis(substituted)-phenols corresponding to the formula

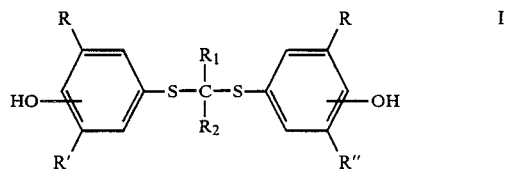

wherein R is tertiary butyl or tertiary pentyl; R' and R" are hydrogen, methyl, ethyl, propyl, butyl, or pentyl, with the proviso that R' and R" are not isopropyl; $R_1$ is hydrogen, methyl or ethyl; and $R_2$ is lower alkyl of from 1 to 6 carbon atoms or keto-substituted lower alkyl of 3 to 6 carbon atoms or $R_2$ is a moiety corresponding to the formula

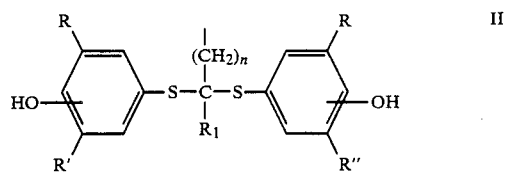

wherein n is 2, 3, or 4 and R, R', R" and $R_1$ are as specified above can be used to inhibit the secretion of IL-1. Such compounds can be administered to animals to inhibit secretion of IL-1; to inhibit or treat IL-1-mediated effects; and to inhibit or treat IL-1-mediated inflammation. The compounds can be administered to inhibit or treat IL-1-mediated effects in conditions such as inflammation, psoriasis, atherosclerosis, and diabetes.

In the method of the invention, an effective amount of one or more of the compounds corresponding to the above formula is administered to an animal, typically to a mammal in need of inhibition of IL-1 secretion, inhibition of IL-1-mediated effects, or inhibition of IL-1-mediated inflammation, in an amount effective to produce such inhibition. The compounds are relatively free from deleterious side effects, at dosages which inhibit IL-1 secretion. The method of the invention can be used to inhibit secretion of IL-1, without concomitant inhibitory effects on concanavalin A induced T lymphocyte and lipopolysaccharide induced B lymphocyte proliferation, or on secretion of the immunological mediators Interleukin 2 and Interleukin 3.

Although the hydroxyl groups can be in either the ortho or para position relative to the thio sulfurs, a preferred group of compounds for use in the method are those wherein the hydroxyl is para to the sulfur. These compounds are 4,4'-substituted alkylidenedithio-bis (2-tert-butyl-6-alkylphenols) corresponding to the formula

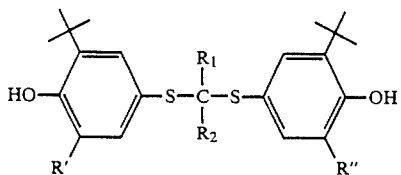

wherein R' and R" are hydrogen, methyl, ethyl, propyl, butyl, or pentyl, with the proviso that R' and R" are not isopropyl; $R_1$ is hydrogen, methyl or ethyl; and $R_2$ is lower alkyl of from 1 to 6 carbon atoms or keto-substituted lower alkyl of 3 to 6 carbon atoms or $R_2$ is a moiety corresponding to the formula

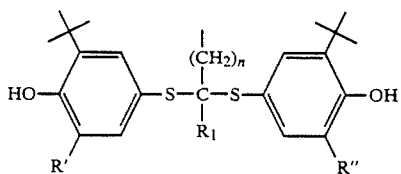

wherein n is 2, 3, or 4 and R', R" and $R_1$ are as specified above.

Preferred compounds for use in the method are those in which all the alkyphenol moieties are the same; those of Formula I wherein both R groups, and R' and R" are all tertiary butyl (tert-butyl or t-butyl) or all tertiary pentyl; those of formula I' wherein R' and R" are both tertiary butyl; those wherein $R_1$ is methyl; and those wherein $R_2$ is methyl or ethyl or propyl. When $R_2$ is keto-substituted alkyl, $R_2$ is preferably a 2-keto alkyl group. When $R_2$ corresponds to Formula II, n is preferably 2 and R' and R" are preferable t-butyl. A particularly preferred compound is the compound corresponding to Formula I' wherein both R groups, R' and R" are tert-butyl; and $R_1$ and $R_2$ are both methyl. This compound is generically known as "probucol". Probucol has been demonstrated to have low toxicity and freedom from deleterious side effects over a wide range of dosages Several of the compounds are described in U.S. Pat. Nos. 3,576,883, 3,786,100, 3,862,332 and 3,897,500 and all the compounds can be made by the methods disclosed in those patents or by analogous methods for preparing mercaptals and mercaptoles, which are well known to organic chemists. In general the compounds are prepared by reacting one molar proportion of the appropriate aldehyde or ketone with two molar proportions of the appropriate thiophenol. The reaction is conveniently carried out by dispersing the thiophenol in an inert organic solvent such as methanol, and adding hydrochloric acid (about 0.05 molar proportion of HCl per molar proportion of thiophenol) as a catalyst. The ketone or aldehyde is then added and the mixture is heated at from about 30° C. to the boiling temperature for from about one to about six hours. When $R_2$ is a moiety of Formula II or II', the aldehyde or ketone reactant is a dialdehyde, keto-aldehyde or diketone, and the molar ratio of the thiophenol reactant is increased to about four molar proportions of thiophenol per molar proportion of the aldehyde or ketone reactant.

The compounds can be administered by conventional routes, oral administration being preferred. The same dosages and routes of administration employed to reduce cholesterol with alkylidene-dithiobis(substituted)-phenols can generally be used in practicing the present invention. The dosage to be employed will vary according to factors such as the species, age, weight and condition of the particular animal being treated, and the particular compound employed. Optimum dosages in particular situations can be determined by conventional dose range finding techniques.

In general, known dosage levels for the compounds, such as those described in U.S. Pat. No. 3,862,332, can be employed. The compounds are preferably administered orally at daily dosages from about one to about 300 milligrams of active ingredient per kilogram of animal body weight. Useful results in inhibition of IL-1 release and alleviation of IL-1 mediated inflammation have been obtained with daily oral dosage of 100 and 200 milligrams per kilogram of animal body weight (mg/kg). The compounds are absorbed slowly from the gastrointestinal tract, and it is frequently desirable to continue administration for several days, or one or two weeks or more to obtain optimum effects.

There is some species variability in response to the compounds used in the method of the invention. For example, in the mouse, probucol gives good inhibition of IL-1 release and antiinflammatory results at a daily dosage of 100 mg/kg, while the results obtained in an antiinflammatory test with rats at that dosage rate were found to be not statistically different from controls. The reduction of IL-1 secretion obtained by administration of 150 mg/kg in rats was less than that seen with 100 mg/kg in mice. The species difference in responsiveness between rats and mice is also observable with respect to cholesterol reduction by probucol, with rats responding poorly or not at all to probucol administered at low dosages which produce good cholesterol reductions in mice or in other species such as dogs and primates.

Reasons for the species differences may include such factors as differences in gastric absorption, different rates of clearance of the compound from the bloodstream, etc. Although the compounds are known to be relatively non-toxic and free of adverse side effects it is generally preferred to administer the compounds at the lowest dosages which produce the desired results. In cases of species variability, mammalian species which are responsive to the compounds are preferred. The species response can be determined by tests for inhibition of IL-1 release, or inhibition of IL-1 mediated effects. The cholesterol-lowering responses of a species to probucol or one of the known cholesterol lowering compounds may also be helpful in predicting species responsiveness or non-responsiveness to the IL-1 related effects of the compounds, inasmuch as the cholesterol lowering response in that species may indicate whether or not significant amounts of the compound are being absorbed or being maintained in the circulatory system.

Although the compounds of the invention, and probucol in particular, are known to be capable of reducing cholesterol, as well as reducing LDL and HDL cholesterol and inhibiting oxidation of LDL cholesterol, it is not necessary for the purposes of the invention that the compounds be administered to an animal in need of the cholesterol-lowering, lipid lowering, or cholesterol oxidation-inhibiting properties of the compounds. Some of the compounds which have useful IL-1 release inhibiting properties have only slight or negligible cholesterol lowering activity. The compounds can be administered to a non-hypercholesterolemic mammal suffering from IL-1-mediated inflammation, with advantageous results in reduction or elimination of the inflammation, or the compounds can be administered to non-hypercholesterolemic animals to alleviate atherosclerotic lesion conditions.

The compounds of the invention can be formulated in conventional pharmaceutically-acceptable carriers to provide unit dosage forms convenient for administration. In general, known dosage forms and carrier materials such as those described in U.S. Pat. No. 3,862,332, can be used. Preferred forms are tablets containing 250 or 500 milligrams of the active compound, such as the probucol tablets presently used to treat hypercholesterolemia.

The invention is further illustrated in the following Examples.

EXAMPLE 1

In vivo Stimulation of IL-1 Release

Male mice (CD-1 strain, Charles River Laboratory) at 6 to 10 weeks of age are used to study the effect of compounds on IL-1 release. The mice are injected intravenously (i.v.) with a zymosan suspension containing 2 milligrams (mg) zymosan in 0.5 milliliters (ml) saline per mouse two weeks before testing. An IL-1-induced acute phase response is then detectable six hours after intravenous injection of lipopolysaccharide (LPS) at a dose of 100 micrograms ($\mu$g) per mouse. (The LPS used is from *Salmonella typhimurium, Re-mutant,* Ribi Immunochemicals, Hamilton, Mo.) The i.v. injection of LPS into the zymosan-treated mice results in an IL-1 induced production of acute phase proteins. One acute phase protein, metallothionein, causes the removal of zinc from the circulation, giving rise to a rapid fall in serum zinc levels which can be measured by atomic absorption.

One group of zymosan-treated mice was administered probucol orally (per os, p.o.) at a daily dosage rate of 100 mg/kg (administered once daily) for 14 days prior to testing. A second group was administered water p.o. and no probucol to serve as a control group.

On the fourteenth day, two subgroups of mice, a water-saline control subgroup and a probucol-saline alone subgroup, were tested for serum zinc levels without administration of LPS. Two other subgroups, a water-LPS alone and a probucol-LPS group, were administered LPS as described above, the water-LPS subgroup having received water and no probucol. Six hours after administration of LPS, peripheral blood was collected from the individual mice and assayed for zinc. The number of mice per group (N) and the results in parts per million (ppm) of zinc are given in the following table.

| Assay | Inhibition of LPS Induced Fall in Serum Zinc (Mean $\pm$ Standard Error of the Mean)(N) | | | |
|---|---|---|---|---|
| | Water p.o.-Saline i.v. Control | Water p.o.-LPS i.v. | Probucol p.o.-Saline i.v. | Probucol p.o.-LPS i.v. |
| Zinc (ppm) | 1.34 $\pm$ 0.06* (11) | 0.59 $\pm$ 0.04 (6) | 1.35 $\pm$ 0.03* (9) | 1.03 $\pm$ 0.29* (5) |

*Significantly different from Control (water p.o., LPS i.v.) $p \leq 0.01$

EXAMPLE 2

The protocol of Example 1 was repeated and the serum zinc levels were again measured.

| Assay | Inhibition of LPS Induced Fall in Serum Zinc (Mean $\pm$ SEM)(N) | | | |
|---|---|---|---|---|
| | Water p.o.-Saline i.v. Control | Water p.o.-LPS i.v. | Probucol p.o.-Saline i.v. | Probucol p.o.-LPS i.v. |
| Zinc (ppm) | 1.24 $\pm$ 0.02 (7) | 0.25 $\pm$ 0.04 (5) | 1.15 $\pm$ 0.05 (9) | 0.63 $\pm$ 0.08* (9) |

*Significantly different from Control (water p.o., LPS i.v.) $p \leq 0.01$

EXAMPLE 3

Treatment of IL-1 Mediated Inflammation

Chronic inflammation was induced in mice by injecting heat-killed *Mycobacterium butyricum* (0.1 ml of a 25 mg/ml suspension in mineral oil) subcutaneously into the hind paws of mice. In this procedure, one hind paw is injected, and the other is left untreated. The injection results in a localized granuloma which develops over about one week, then slowly declines over the next several weeks. The swelling of the granulomatous paws is measured volumetrically and compared to the uninjected paws. This procedure was performed with four groups of mice, with paw swelling measurements being made one, two, and five weeks after injection of *Mycobacterium butyricum*. One group was administered water to serve as a control. The other three groups were orally administered a test compound, prednisone, probucol or ibuprofen, at a dosage rate of 100 mg/kg per day, starting on the day of granuloma induction. The mean paw swelling expressed as a percentage increase in volume ($\pm$SEM) compared to the contralateral uninjected paw, the percentage reduction of swelling obtained with the test compounds, the level of statistically significant difference from the results with the control group (p value) and the number of mice per group (N) are set out in the following table.

| | Reduction of *Mycobacterium butyricum* Induced Paw Swelling | | | | |
|---|---|---|---|---|---|
| | Time | Control | Prednisone | Probucol | Ibuprofen |
| Swelling (Mean $\pm$ SEM) | 1 Week | 161.7 $\pm$ 13.1 — | 37.2 $\pm$ 6.9 77% | 110.3 $\pm$ 12.2 32% | 99.6 $\pm$ 12.8 38% |
| % Reduction p value (N) | | —(10) | $\leq$0.01 (10) | $\leq$0.01 (10) | $\leq$0.01 (10) |
| Swelling (Mean $\pm$ SEM) | 2 Weeks | 164.0 $\pm$ 7.5 — | 70.2 $\pm$ 12.2 57% | 89.0 $\pm$ 11.7 46% | 122.4 $\pm$ 11.6 25% |
| % Reduction p value (N) | | —(10) | $\leq$0.01 (9*) | $\leq$0.01 (10) | $\leq$0.05 (10) |
| Swelling | 5 | 105.1 $\pm$ 10.1 | 61.1 $\pm$ 7.3 | 71.8 $\pm$ 5.7 | 91.1 $\pm$ 10.7 |

-continued

| | Reduction of *Mycobacterium butyricum* Induced Paw Swelling | | | | |
|---|---|---|---|---|---|
| | Time | Control | Prednisone | Probucol | Ibuprofen |
| (Mean ± SEM) % Reduction p value (N) | Weeks | —(10) | 42% ≦0.01 (8**) | 32% ≦0.05 (10) | 13% >0.05 (10) |

*One mouse died after one week.
**One mouse died after two weeks.

EXAMPLE 4

Ex Vivo Inhibition of IL-1 Secretion

Peritoneal macrophages obtained from CD-1 mice were collected and washed once with RPMI-1640 medium (GIBCO, Grand Island, N.Y.) continuing 100 Units/ml penicillin, 100 µg/ml streptomycin and 25 µg/ml fungizone (GIBCO, Grand Island, N.Y.). Cells were suspended at $6 \times 10^6$ cells per ml, and one ml aliquots were plated into 6well flat bottom plates. After one hour incubation at 37° C. in a humidified air chamber containing 5% $CO_2$, non-adherent cells were removed and 1 ml RPMI medium (with or without lipopolysaccharide—100 µg/well) was added to each well. As discussed above in Example 1, LPS stimulates macrophages to release IL-1. Incubation was continued for 6 hours, after which the culture supernatant was collected and filtered through 0.22 micrometer Acrodisc filters (Gelman, Ann Arbor, Mich.). The fluid was stored at a temperature of −70° C. until assayed for IL-1 activity.

IL-1 activity was determined by the C3H/HeJ thymocyte proliferation assay of Mizel et al., *J.Immunol.* 120:1497 (1978). In this procedure, thymocytes of C3H/HeJ mice are incubated with the macrophage culture supernatant in the presence of phytohemagglutinin, and pulsed by incubation with 3H-thymidine. The cells are then harvested and radioactivity is determined by liquid scintillation counting. IL-1 activity was expressed as units defined according to Mizel et al, *J.Immunol.* 120:1497 (1978).

Compounds were tested in this procedure by oral administration to CD-1 mice 40, 24 and 16 hours prior to collection of peritoneal macrophages. The dosage used was 100 mg/kg.

In one test, peritoneal macrophages from untreated, control mice, gave results of 677±59 IL-1 units/ml, while the probucol treated group gave assay results of only 171±15 IL-1 units/ml, indicating that a 75% inhibition of IL-1 secretion was obtained with oral administration of probucol. In a second test the control group of mice gave 960±42 IL-1 units/ml, as compared to 153±18 units/ml in the probucol-treated group, a reduction of 84%. In a third test, the control group was 779±90 IL-1 units/ml, while the probucol group assay was 114±13 IL-1 units/ml, indicating that an 86% inhibition of IL-1 secretion was obtained by the administration of probucol. In a fourth test rats were used as the test animals, and the probucol dosage was 150 mg/kg. In this test, the control group gave 271±6 units/ml and the probucol-treated rats gave 187±15 units/ml, a reduction of 31 per cent. The above results are expressed as the mean ± the standard deviation of the mean. All probucol results were significantly different from control at p <0.01.

EXAMPLE 5

The procedure of Example 4 was repeated using different alkylidenedithiobis(substituted)phenol compounds. The percentage reduction of IL-1 secretion obtained with the compounds (rounded to the nearest percent) is set out in the following table.

| | | Reduction of IL-1 Secretion | | | |
|---|---|---|---|---|---|
| R | R' and R" | $R_1$ | $R_2$ | OH to S | Per Cent Reduction of IL-1 Secretion |
| t-butyl | t-butyl | methyl | n-propyl | para | 55 |
| t-butyl | t-butyl | H | ethyl | para | 54 |
| t-butyl | t-butyl | ethyl | ethyl | para | 96 |
| t-butyl | t-butyl | methyl | 2-keto-propyl | para | 68 |
| t-butyl | t-butyl | methyl | n-hexyl | para | 90 |
| t-butyl | t-butyl | methyl | Formula II moiety; n = 2, R,R' and R" = tert-butyl, RI = methyl | para | 92 |
| t-butyl | methyl | H | methyl | para | 92 |
| t-butyl | methyl | methyl | ethyl | para | 72 |
| t-butyl | methyl | methyl | n-butyl | para | 45 |
| t-pentyl | t-pentyl | methyl | methyl | para | 65, |
| t-butyl | t-butyl | methyl | methyl | ortho | 89 |

*Indicates the position of the hydoxyl group on the phenol relative to the thio sulfur.

EXAMPLE 6

Effect on Secretion of Interleukins 2 and 3 and Effects on Lymphocyte Proliferation IL-2 is required for the induction of T lymphocytes and for clonal expansion of T lymphocytes; and IL-3 is a growth factor for granulocytes. The effect of probucol on secretion of Interleukin 2 and Interleukin 3 (IL-2 and IL-3) was studied in a procedure similar to that described by Bowlin et al., *Cellular Immunology*, 98, 341-350 (1986), using spleen cells from mice dosed with probucol as per Example 4 and cell stimulation with concanavalin-A.

When the spleen cells from probucol-dosed mice were stimulated with concanavalin-A in vitro, the cells secreted no less IL-2 and IL-3 than did normal spleen cells (from mice not treated with probucol). These results indicate that the probucol treatment does not inhibit the induction, synthesis and secretion of the immunological mediators IL-2 and IL-3.

In other tests, the mitogens lipopolysaccharides (LPS) and concanavalin A were used to induce proliferation of B and T lymphocytes, respectively, of both normal, untreated mouse spleen cells, and spleen cells from mice which had been administered probucol (100 mg/kg orally given 40, 24, and 16 hours prior to the experiment). The proliferation of the spleen cells from probucol-treated mice was not inhibited as compared with the control, normal spleen cell cultures, indicating that there was no inhibitory effect on mitogen-induced spleen cell proliferation at a probucol dosage which inhibits IL-1 release.

What is claimed is:

1. A method of inhibiting the release of interleukin-1 in animals which comprises administering to an animal in need thereof an effective amount of a compound corresponding to the formula

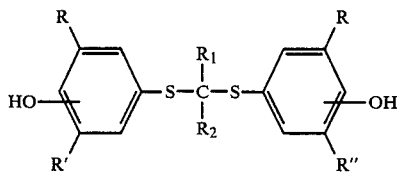

wherein R is tertiary butyl or tertiary pentyl; R' and R" are hydrogen, methyl, ethyl, propyl, butyl, or pentyl, with the proviso that R' and R" are not isopropyl; $R_1$ is hydrogen, methyl or ethyl; and $R_2$ is lower alkyl of from 1 to 6 carbon atoms or keto-substituted lower alkyl of 3 to 6 carbon atoms or $R_2$ is a moiety corresponding to the formula

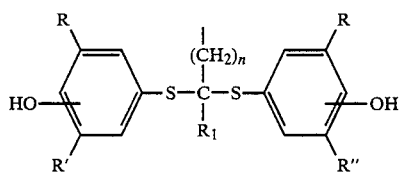

wherein n is 2, 3, or 4.

2. Method of claim 1 wherein R, R' and R" all represent tertiary butyl.

3. Method of claim 1 wherein the compound corresponds to the formula

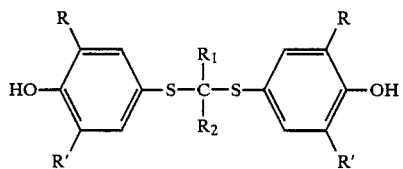

wherein R is tertiary butyl or tertiary pentyl; R' and R" are hydrogen, methyl, ethyl, propyl, butyl, or pentyl, with the proviso that R' and R" are not isopropyl; $R_1$ is hydrogen, methyl or ethyl; and $R_2$ is lower alkyl of from 1 to 6 carbon atoms or keto-substituted lower alkyl of 3 to 6 carbon atoms or $R_2$ is a moiety corresponding to the formula

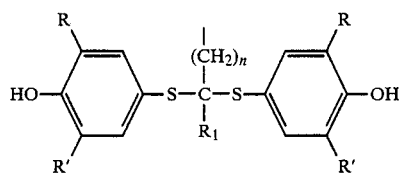

wherein n is 2, 3, or 4.

4. Method of claim 2 wherein R is tertiary butyl, $R_1$ is methyl and $R_2$ is lower alkyl of from 1 to 3 carbon atoms.

5. Method of claim 4 wherein the compound is probucol.

6. Method of claim 1 wherein the animal is a non-hypercholesterolemic mammal.

7. Method of claim 1 wherein the animal is in need of inhibition of an interleukin-1 mediated effect which is inflammation, and wherein the compound is administered in an amount effective to reduce the inflammation.

8. Method of claim 1 wherein the animal is in need of inhibition of an interleukin-1 mediated effect which is diabetes.

9. Method of claim 1 wherein the animal is in need of inhibition of an interleukin-1 mediated effect which is psoriasis.

10. Method of claim 1 wherein the animal is non-hypercholesterolemic and in need of inhibition of an interleukin-1 mediated effect which is atherosclerosis.

11. Method of claim 10 wherein the animal is a non-hypercholesterolemic mammal and wherein the compound is probucol.

12. Method of claim 1 wherein the compound corresponds to the formula

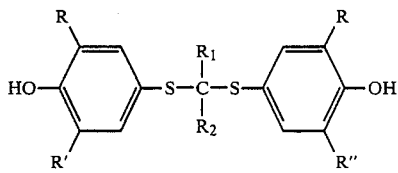

wherein R is tertiary butyl or tertiary pentyl; R' and R" are hydrogen, methyl, ethyl, propyl, butyl, or pentyl, with the proviso that R' and R" are not isopropyl; $R_1$ is hydrogen, methyl or ethyl; and $R_2$ is lower alkyl of from 1 to 6 carbon atoms or keto-substituted lower alkyl or 3 to 6 carbon atoms.

13. Method of claim 12 wherein $R_1$ is methyl and $R_2$ is lower alkyl of from 1 to 3 carbon atoms.

14. Method of claim 12 wherein R, R' and R" are all tertiary butyl, $R_1$ is methyl and $R_2$ is n-propyl.

15. Method of claim 12 wherein R, R' and R" are all tertiary butyl, $R_1$ is methyl and $R_2$ is 2-ketopropyl.

16. Method of claim 12 wherein R, R' and R" are all tertiary butyl, $R_1$ is hydrogen and $R_2$ is ethyl.

17. Method of claim 12 wherein the animal is a non-hypercholesterolemic mammal and wherein the compound is probucol.

18. A method of treating inflammation in animals which comprises administering to an animal in need thereof an effective amount to alleviate inflammation of a compound corresponding to the formula

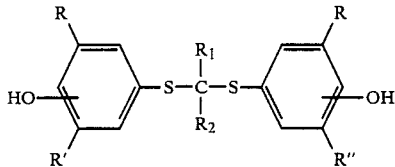

wherein R is a tertiary butyl or tertiary pentyl; R' and R" are hydrogen, methyl, ethyl, propyl, butyl, or pentyl, with the proviso that R' and R" are not isopropyl; $R_1$ is hydrogen, methyl or ethyl; and $R_2$ is lower alkyl of from 1 to 6 carbon atoms or keto-substituted lower alkyl of 3 to 6 carbon atoms or $R_2$ is a moiety corresponding to the formula

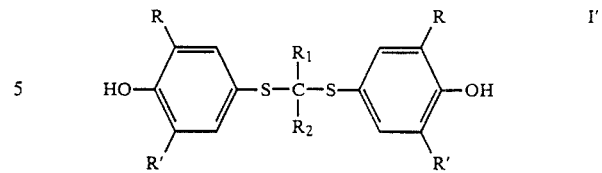

wherein R is tertiary butyl; R' and R" are hydrogen, methyl, ethyl, propyl, butyl, or pentyl, with the proviso that R' and R" are not isopropyl; $R_1$ is hydrogen, methyl or ethyl; and $R_2$ is lower alkyl of from 1 to 6 carbon atoms or keto-substituted lower alkyl of 3 to 6 carbon atoms or $R_2$ is a moiety corresponding to the formula

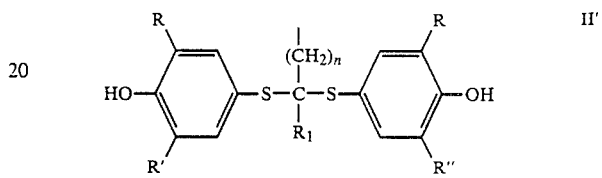

wherein n is 2, 3 or 4.

20. Method of claim 19 wherein $R_1$ is methyl and $R_2$ is methyl, ethyl or propyl.

\* \* \* \* \*

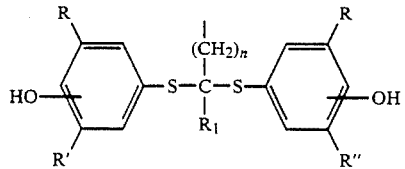

wherein n is 2, 3, or 4.

19. Method of claim 18 wherein the compound corresponds to the formula

UNITED STATES PATENT AND TRADEMARK OFFICE
CERTIFICATE OF CORRECTION

PATENT NO. : 4,975,467
DATED : December 4, 1990
INVENTOR(S) : GEORGE KU AND NIALL DOHERTY It is certified that error appears in the above-identified patent and that said Letters Patent is hereby corrected as shown below:

```
In Column 7, Line 64, the patent reads "<0.01" and should read "≤0.01"
In Column 9, Line 53, the patent reads "I'" and should read "II'".
```

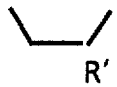

and should read

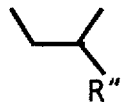

Signed and Sealed this

Fourth Day of August, 1992

Attest:

DOUGLAS B. COMER

*Attesting Officer*     Acting Commissioner of Patents and Trademarks